United States Patent [19]

Cherubim et al.

[11] 3,988,384

[45] Oct. 26, 1976

[54] CONVERSION OF OLEFINS USING IMPROVED CATALYSTS

[75] Inventors: Martin Cherubim, Rheinkamp-Eick; Elmar Wilms, Kamp-Lintfort; Hans Arendsen, Homberg, all of Germany

[73] Assignee: Deutsche Texaco Aktiengesellschaft, Hamburg, Germany

[22] Filed: Dec. 3, 1974

[21] Appl. No.: 529,182

[30] Foreign Application Priority Data

Dec. 7, 1973 Germany............................ 2360981

[52] U.S. Cl. ...................... 260/683 D; 260/666 A; 260/677 R; 260/680 R
[51] Int. Cl.² ......................................... C07C 3/62
[58] Field of Search ........ 260/683 D, 666 A, 677 R, 260/680 R

[56] References Cited

UNITED STATES PATENTS

| | | | |
|---|---|---|---|
| 3,586,731 | 6/1971 | Heckelsberg | 260/683 |
| 3,637,891 | 1/1972 | McGrath et al. | 260/683 |
| 3,658,927 | 4/1972 | Crain et al. | 260/683 |

*Primary Examiner*—D. Horwitz
*Assistant Examiner*—C. E. Spresser
*Attorney, Agent, or Firm*—T. H. Whaley; C. G. Ries; Robert Knox, Jr.

[57] ABSTRACT

Supported olefin conversion catalysts are activated by a method which comprises calcining the catalyst, impregnating the calcined catalyst with an alcoholic solution of an alkali metal salt, an alkali metal base or an alkali metal alcoholate and then recalcining the catalyst.

10 Claims, No Drawings

CONVERSION OF OLEFINS USING IMPROVED CATALYSTS

The present invention relates to a process for improving supported catalysts and to a process for their use in the conversion of olefins. It is known to convert olefins in the gaseous phase into olefins having longer or shorter carbon chains than the olefin charge material using solid catalysts containing, for example, molybdenum, tungsten, niobium, tantalum, vanadium, cobalt, nickel, rhenium, and the like as the active ingredients and aluminum hydroxide or aluminum oxide, kieselguhr, pumice, titanium oxide, activated carbon and the like as the support. As disclosed in German Pat. No. 1,668,999, the addition of from 0.02 to 5 weight percent, preferably 0.1 to 1 wt. %, of alkali metal or alkaline earth metal to a disproportionation catalyst such as rhenium heptoxide on an aluminum oxide base, reduces polymerization and improves selectivity. These catalysts are prepared by impregnating the bases or supports with aqueous alkali metal salt solutions, drying, calcining, depositing the active metals thereon and, optionally, repeating the calcining treatment. Unfortunately, these catalysts are of low crush strength and hence are unsuitable for commercial scale conversion of olefins using fixed beds of catalysts. In addition, these catalysts are unsuitable for olefin conversion using the fluidized bed type of operation. If the active metals are precipitated, for example, on aluminum oxide or aluminum hydroxide, kieselguhr and the like, and an aqueous solution of alkali metal salts or bases is added, catalysts so prepared have unsatisfactory crush strength. If these catalysts first are dried and calcined and then subjected to post-alkalization with aqueous alkali metal salt solutions, no improvement in the crush strength of the catalysts is attained.

It is therefore an object of the present invention to provide a process for the alkalization of olefin conversion catalysts, said process serving to impart to these catalysts sufficient hardness to permit their use in the commercial scale disproportionation of olefins, especially using fixed beds of catalysts, and a further increased activity and selectivity.

It has now been found that the hardness and hence the commercial utility including the regenerability, activity and selectivity of supported disproportionation catalysts may be considerably improved by post-alkalization by impregnating the supported catalysts, which have been calcined at temperatures ranging from about 300° to 800° C., with alcoholic solutions of alkali metal salts or bases or alkali metal alcoholates and then subjecting them to a post-calcination treatment for 0.5 to 8 hours at temperatures in the range of from about 400° to 700° C. The concentrations of the alcoholic solutions may range from 1 to 15 weight percent, preferably from 5 to 10 wt. %. The catalysts prepared according to this invention contain from 0.01 to 15 wt. %, preferably from 0.1 to 8 wt. % of alkali metal preferably sodium and potassium.

The calcination is best conducted in a stream of inert gas, air and/or oxygen.

Suitable solvents for the alkali metal compounds include monohydric, polyhydric as well as primary, secondary and/or tertiary alcohols. It is also possible to blend the alcohols with other organic solvents such as ketones, aromatics and the like.

An important feature in the process of our invention is that the supported catalysts have been calcined prior to the impregnation with the alcoholic solutions of the alkali metal salts, bases or alcoholates as the impregnation of non-calcined catalysts, even when subjected to post-calcination, will not yield the desired effect.

In the alkalization process the catalysts may be employed either in powder or particle form as well as in the form of pellets or extrudates. They may have been formulated, for example, from the afore-mentioned active metals and supporting substances. Catalysts formulated with molybdenum, tungsten and cobalt as the active metals and $Al_2O_3$ as the catalyst base have been found to be particularly suitable.

The catalysts may be employed to convert both aliphatic monoolefins and polyolefins as well as cyclic olefins. The olefins may be used both in pure form and in the form of mixtures. Saturate hydrocarbons as well as gases inert under reaction conditions may be added as diluents.

Owing to their great firmness the olefin conversion catalysts of this invention also have excellent regeneration properties and hence an excellent lifetime.

The process of this invention may be better understood from the following example which is given for illustrative purposes only.

EXAMPLE 1,500 ml of water are added with stirring to 1,500 grams of aluminum secondary butylate within a period of 30 minutes, and the stirring is continued for one hour. Steam is then introduced into the mixture for the purpose of separating the alcohol, the steam being introduced in an amount sufficient for the layers to separate. Thereafter, stirring is continued for additional 30 minutes with the addition of steam, and the $Al(OH)_3$ which has formed is filtered. The obtained $Al(OH)_3$ paste then is adjusted to an $Al_2O_3$ content of 25 wt. %.

800 grams of the so produced 25% $Al(OH)_3$ paste is kneaded for 30 minutes in a kneader, and 33.6 grams of ammonium molybdate dissolved in 100 ml of water are added portion-wise. After that, the mass is kneaded for another hour for good homogeneity. Then, 32.6 grams of cobalt nitrate dissolved in 20 ml of water, are added portion-wise, the catalyst mass is kneaded for one hour, formed into small particles, dried for 4 hours at 120° C. and calcined for four hours in a tube with a stream of air passing therethrough at a rate of 20 liters per hour and at a temperature of from 530° to 550° C.

The activation of the calcined catalyst according to this invention is achieved by dissolving 16 grams of KOH in 200 ml methanol, impregnating the catalyst with this solution, drying and subjecting it once more to calcination for four hours in a stream of dry air (20 liters/hr.) at 550° C. Upon completion of this treatment, the catalyst has the following composition, by weight:

| | | |
|---|---|---|
| $Al_2O_3$ | — | 79.7% |
| $MoO_3$ | — | 11.0% |
| CoO | — | 3.5% |
| $K_2O$ | — | 5.8% |

The activity of the catalyst is tested by filling 190 ml of same into a tube having a diameter of 2.4 cm. Eighty liters of propylene per hour are passed through the catalyst at a temperature of 175° C., with a 52.6% disappearance of said propylene, the selectivity for the conversion to other olefins being above 99 percent. The obtained olefin mixture has the following composition by weight:

| | | |
|---|---|---|
| ethylene | — | 15.2% |
| tert.-butylene-(2) | — | 19.6% |
| cis-butylene-(1) | — | 12.8% |
| butylene-(1) | — | 1.6% |
| pentenes | — | 3.1% |
| polymers | — | 0.3% |
| propylene | — | 47.4% |

The reaction conditions for the conversion of olefins are well known and form no part of our invention.

Similar results are obtained using other catalysts in which the active metals are selected from Groups V, VI, VII and VIII of the Periodic Table such as tantalum, vanadium, niobium, tungsten, rhenium and nickel. In this connection, the use of the term active "metals," when referring to the catalysts, is intended to include metal compounds such as the oxides.

Various modifications of the invention as hereinbefore set forth may be made without departing from the spirit and scope thereof, and therefore, only such limitations should be made as are indicated in the appended claims.

The embodiments of the invention in which an exclusive property or privilege is claimed are defined as follows:

1. In a process for the disproportionation of olefins which comprises contacting an olefin at a temperature between about 100° and 300° C. with a disproportionation catalyst, the improvement which comprises contacting said olefin with a disproportionation catalyst prepared by a method which comprises impregnating a refractory inorganic oxide support with a compound of at least one catalytically active metal, calcining the impregnated support at a temperature between 300° and 800° C., impregnating the calcined catalyst with an alcoholic solution of a member of the group consisting of alkali metal salts, alkali metal bases and alkali metal alcoholates and recalcining the catalyst at a temperature between 400° and 700° C.

2. The process of claim 1 in which the catalyst comprises a Group VI metal compound and a Group VIII metal compound on a support comprising alumina.

3. The process of claim 2 in which the metal compounds are oxides.

4. The process of claim 1 in which the disproportionation is carried out in the presence of an inert diluent gas.

5. The process of claim 4 in which the inert gas is a saturated hydrocarbon.

6. The process of claim 1 in which the olefin feed comprises an aliphatic monoolefin.

7. The process of claim 1 in which the olefin feed comprises an aliphatic polyolefin.

8. The process of claim 1 in which the olefin feed comprises a cyclic olefin.

9. The process of claim 1 in which the olefin feed comprises propylene and the disproportionated product comprises ethylene and butylene.

10. The process of claim 1 in which the catalyst contains between 0.01 and 15 wt. % alkali metal.

* * * * *